United States Patent [19]
Cerny et al.

[11] Patent Number: 5,609,837
[45] Date of Patent: Mar. 11, 1997

[54] DISINFECTION APPARATUS

[76] Inventors: David E. Cerny, 1451 Sandford Trail, Lilburn, Ga. 30247; Christopher J. Brooks, 13 Meadow La., Glen Head, N.Y. 11545

[21] Appl. No.: 515,782

[22] Filed: Aug. 16, 1995

[51] Int. Cl.⁶ .................... A61L 2/18; B65D 51/16; B65D 41/28
[52] U.S. Cl. .................... 422/301; 422/113; 206/5.1; 220/203.13; 134/901; 215/354
[58] Field of Search .................... 422/113, 300, 422/301; 206/5.1; 220/203.11, 203.12, 203.13, 303, 366.1; 134/901; 215/354, 356

[56] References Cited

U.S. PATENT DOCUMENTS

| | | | |
|---|---|---|---|
| 3,005,455 | 10/1961 | Poitras et al. | 215/354 X |
| 3,912,451 | 10/1975 | Gaglia | 422/30 |
| 4,011,941 | 3/1977 | Parsons | 206/5.1 |
| 4,483,439 | 11/1984 | Steigerwald et al. | 220/203.11 X |
| 4,637,919 | 1/1987 | Ryder et al. | 422/300 |
| 4,750,610 | 6/1988 | Ryder | 206/5.1 |
| 4,807,750 | 2/1989 | Ryder et al. | 206/5.1 |
| 4,890,729 | 1/1990 | Ranalletta | 206/5.1 |
| 4,956,156 | 9/1990 | Kanner et al. | 422/300 |
| 4,981,657 | 1/1991 | Ryder | 422/310 |
| 4,996,027 | 2/1991 | Kanner | 422/113 |
| 5,196,174 | 3/1993 | Cerolo et al. | 422/300 |
| 5,250,266 | 10/1993 | Kanner | 422/113 |
| 5,275,287 | 1/1994 | Thompson | 215/354 X |
| 5,346,083 | 9/1994 | Song et al. | 215/354 X |
| 5,388,686 | 2/1995 | Kanner et al. | 206/5.1 |
| 5,421,470 | 6/1995 | Dudzik | 215/354 X |

FOREIGN PATENT DOCUMENTS 9209942  11/1992  WIPO.

Primary Examiner—Robert J. Warden
Assistant Examiner—E. Leigh Dawson
Attorney, Agent, or Firm—Edward McC. Roberts; R. Scott Meece; Michael U. Lee

[57] ABSTRACT

A disinfection apparatus including a container; a cap having an article-retainer, a and a catalytic element-retainer means affixed thereto; and a catalytic element. The disinfection apparatus has particular utility in the disinfection of contact lenses with hydrogen peroxide solutions. Also disclosed are venting and sealing components, catalytic elements, molded article-retaining assemblies, and catalytic element formation methods.

14 Claims, 7 Drawing Sheets

DISINFECTION APPARATUS

BACKGROUND OF THE INVENTION

1. Field of the Invention

This invention relates broadly to devices for disinfection. In a preferred embodiment, the invention relates to devices for disinfection of contact lenses.

2. Description of the Related Art

Contact lenses provide the consumer with an exceptionally convenient and comfortable alternative to conventional eyeglasses. However, proper maintenance of contact lenses involves periodic lens sterilization or disinfection to eliminate harmful bacteria and fungi, and cleaning to remove deposits such as proteins or lipids which adhere to the lens. In order to clean and disinfect contact lenses, a wide variety of devices have been developed.

A particularly efficacious method of disinfecting contact lenses is by a chemical treatment of the lenses with a hydrogen peroxide solution, as described in U.S. Pat. No. 3,912,451, issued to Gaglia, Jr., Oct. 14, 1975. In a typical lens disinfecting apparatus, contact lenses are placed in hydrogen peroxide solution inside a container. The container is sealed (e.g., by threads on the container mating with threads on a cap) for a predetermined period of time to sufficiently disinfect the lenses, with the seal preventing liquid spillage resulting from container movement.

Although hydrogen peroxide is highly effective in disinfecting contact lenses, hydrogen peroxide must be removed from lenses prior to placing the lenses in a patient's eye in order to avoid patient discomfort. One method of removing hydrogen peroxide involves contacting the hydrogen peroxide with a platinum catalyst, thereby rapidly decomposing the hydrogen peroxide into water and gaseous oxygen. Liberated gaseous oxygen resulting from the peroxide decomposition generates internal pressure in the disinfecting container Which must be vented. In order to alleviate this pressure, a variety of venting means have been developed. Also, a number of catalytic elements and lens retaining assemblies have been developed. The catalytic elements disclosed in the art have primarily been some form of platinum-coated disk-shaped elements.

For example, U.S. Pat. No. 4,011,941, issued to Parsons on Mar. 15, 1977, discloses a contact lens sterilization container which includes a hollow cylindrical chamber having two opposing openings which are sealed by two caps. One cap includes a convoluted catalytic reactor which is friction-retained on the cap. The catalyst is essentially a disc-shaped element with protuberances extending therefrom. The other cap includes a stem with contact lens holders and a resealable venting means. The venting means is an O-ring positioned in an annular groove passageway from the interior of the container to the exterior surroundings. The O-ring acts as a pressure release valve when oxygen is produced by the decomposition of peroxide in the presence of the catalyst.

U.S. Pat. No. 4,637,919, issued to Ryder, et al., Jan. 20, 1987, discloses a contact lens cleaning container and mating cap, where the cap includes a filter assembly positioned in a vent passageway. The filter assembly includes a hydrophobic membrane which continuously vents the gas generated within the container during the decomposition of peroxide. The pores in the hydrophobic membrane are sufficiently small to inhibit liquid leakage from the container. The catalyst used is the same or analogous to the catalyst disclosed in U.S. Pat. No. 4,011,941.

U.S. Pat. No. 4,750,610, issued to Ryder, Jun. 14, 1988, discloses a disinfecting container which is affixed to a cap via loose threading. The cap includes a resiliently deflectable flange which acts as a check valve in conjunction with the container. In operation, the cap flange is typically in a closed position, i.e., the flange is positioned immediately adjacent a portion of the container, thereby preventing liquid leakage. When excess internal pressure develops, the cap flange deflects, allowing gas to pass through the loosely threaded container-cap connection to the outside of the container. The catalyst used is the same or analogous to the catalyst disclosed in U.S. Pat. No. 4,011,941.

U.S. Pat. No. 4,956,156, issued to Kanner, et al., Sep. 11, 1990, discloses a disinfecting system which includes a cap having a bore. A post is positioned in the bore with a resiliently-deflectable diaphragm positioned around the post. The diaphragm-post seal prevents liquid leakage, while allowing gas to pass upon deflection of the diaphragm when sufficient internal pressure develops.

U.S. Pat. No. 4,996,027, issued to Kanner, Feb. 26, 1991, discloses a disinfecting system which includes a container and cap connected by threading. A self-reseating unitary gasket is positioned between the cap and container to provide a liquid-tight seal. Increased internal pressure causes the gasket to unseat, at least partially, allowing gas to pass between the cap and container connection to the environment.

U.S. Pat. No. 5,196,174, issued to Cerola, et al., on Mar. 23, 1993, discloses a structure for removably mounting a catalyst between the contact lenses holders. The catalyst is a disc which is defined as a generally flat, disc-like member with a pattern of recesses and ridges formed on either face or surface thereof. The advantage of the design is that the catalyst may be removed and replaced by a user as the catalytic agent becomes exhausted from use.

U.S. Pat. No. 5,250,266, issued to Kanner, Oct. 5, 1993, discloses a lens disinfecting apparatus, including a container and a cap, in which gas is vented through a type of check valve in the cap. The check valve includes a disc having a linear slit therethrough. The slit generally provides a liquid-impermeable barrier, but when internal pressure is generated, the slit opens to allow gas to pass to the environment.

The previously-described patents describe various alternatives for peroxide-based lens cleaning/disinfecting devices. However, there is a need to provide a less complicated system, both from a manufacturing perspective and from an operational perspective. In addition, there is a need for catalyst elements which are less expensive to manufacture and which provide improved fluid flow profiles during peroxide decomposition. Further, there is a need for improved means for allowing internally generated gas to vent from the disinfection device. There is also a need to improve the cap and lens retaining assembly.

SUMMARY OF THE INVENTION

An object of the invention is to provide a disinfection device which may be manufactured with less complexity than prior art devices.

Another object of the invention is to provide a catalytic element which has improved fluid flow profiles.

A further object of the invention is to provide a catalytic element which is less complex and less costly to manufacture than prior art catalytic elements.

Yet another object of the invention is to provide an improved vent means for a disinfection device which generates gas during operation.

An additional object of the present invention is to provide a contact lens disinfection system having improved venting means, an improved catalytic element, and improved ease of manufacturing.

One embodiment of the present invention is a catalytic element for a disinfection device. The catalytic element includes a catalyst substrate having a base portion, a side wall portion extending from the peripheral edge of the base portion, with the portions defining an inner concave surface and an outer convex surface, and a means for affixing the catalytic element to a catalytic element supporting member. The catalytic element further includes a coating of catalytic material deposited on at least a portion of a surface of the catalyst substrate, which catalytic material catalyzes the decomposition of a disinfectant species in solution. A preferred catalytic material is platinum and a preferred disinfectant is hydrogen peroxide.

Another embodiment of the present invention is a sealing and venting component for a device which generates internal gas pressure during operation. The sealing and venting component provides a substantially liquid impermeable seal which vents internally generated gas at a certain pressure differential. The sealing and venting component includes a housing having an internal and an external surface, and at least two elongated rims extending outwardly from the external surface a distance which is sufficient for the rims to contact the internal surfaces of the cylindrical container to establish a sealed chamber with said container. The rims are sufficiently flexible to at least partially deform to allow gas to vent from said chamber. The rims are sufficiently resilient to return to a position of contact with the container after venting, thereby reestablishing said sealed chamber.

A further embodiment of the present invention is an assembly for use in a disinfection container. The assembly is inexpensive and simple to manufacture and assemble, and may be easily recycled. The assembly includes (a) a cap including a means for affixing the cap to the container, (b) an elongated support member affixed to the cap, (c) sealing means affixed to the elongated support member, with the sealing means being capable of forming a substantially liquid impermeable chamber with said container, (d) lens-retaining means affixed to the elongated support member, (e) catalytic element-retaining means affixed to said elongated support member; and a catalytic element retained within the catalytic element-retaining means.

Yet another embodiment of the present invention is a disinfection device, which is particularly useful in the disinfection of contact lenses. The disinfection device includes (a) a container adapted to receive a disinfecting solution; (b) a cap adapted to be releasably affixed to the container at the open end; (c) an elongated support member extending into the container and being affixed to the cap; (d) an article-retaining means affixed to the elongated member; (e) a sealing means affixed to said elongated member; and (f) a catalytic element affixed to the elongated member. The sealing means is at least partially deformable, such that internal gas generated within said container will vent to a point outside said container.

Still another embodiment of the invention is a process for making a catalytic element. The process includes the steps of (a) feeding a continuous sheet of substrate material into a vacuum forming chamber, (b) vacuum forming a desired catalytic element shape in the substrate material, (c) feeding the continuous sheet into a coating chamber, (d) coating at least one surface of the shaped catalytic element substrate to form a catalytic element, and (e) removing a catalytic element from the sheet.

DESCRIPTION OF THE PREFERRED EMBODIMENTS

The invention has utility in the disinfection of articles, such as ophthalmic lenses, which require routine disinfection procedures to be performed by consumers. "Disinfection", as used herein, refers broadly to deactivating, killing, or removing microorganisms from an article, and is sometimes referred to as sterilization or cleaning. The disinfection processes which are useful in accordance with the present invention are those in which a gas is liberated during or after the disinfection process, for example, by decomposition of the disinfectant. The invention finds particular utility in the disinfection of contact lenses with peroxide, concurrently with or followed by catalytic decomposition of the peroxide into water and gaseous oxygen.

Figure 1:
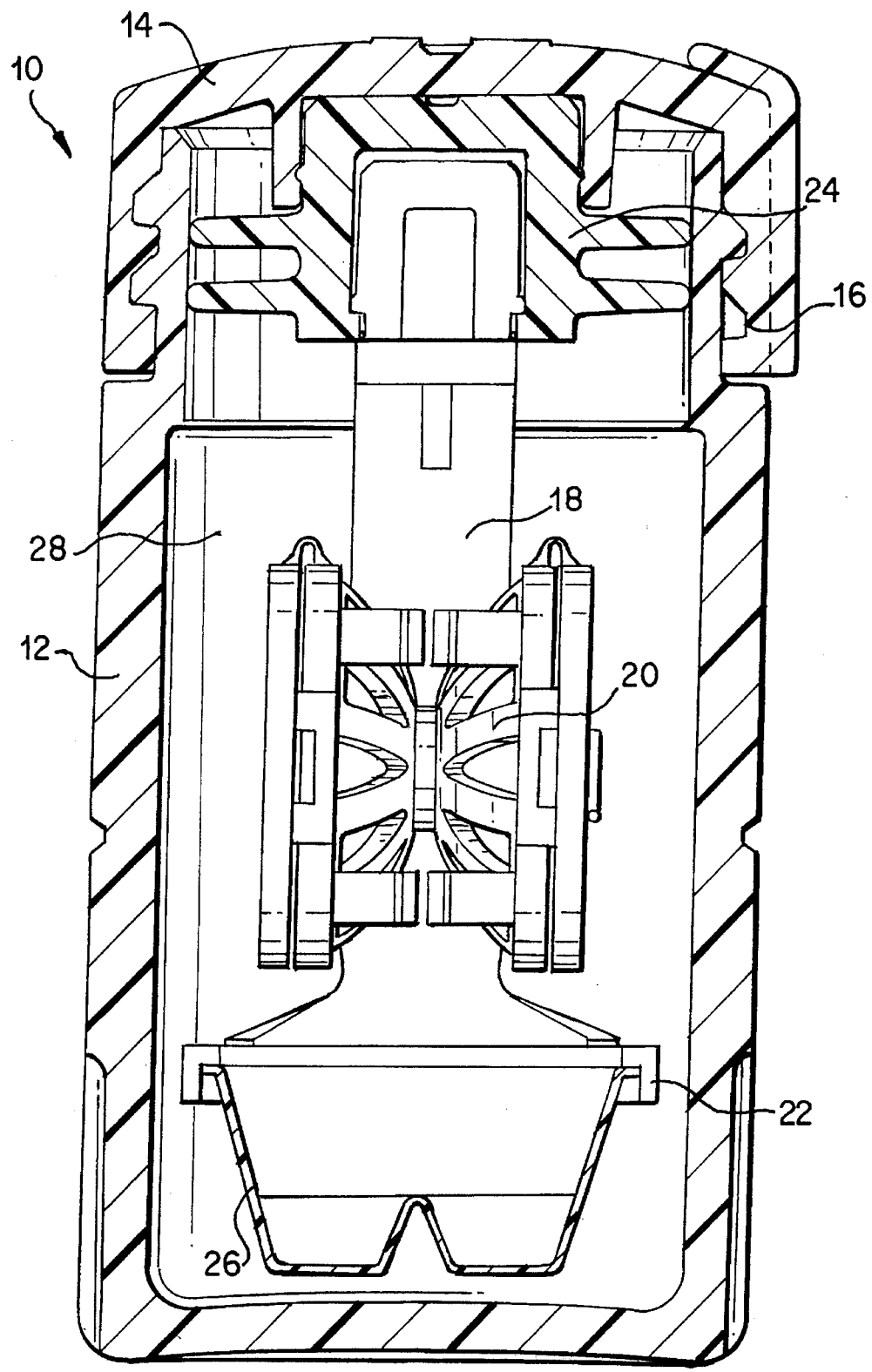
FIG. 1 is a side sectional view of one embodiment of a contact lens disinfection apparatus of the present invention.

The invention may be easily understood with reference to the drawings. FIG. 1 is a side sectional view of one embodiment of a disinfection apparatus of the present invention. Disinfection apparatus 10 includes container 12 which is adapted to receive a disinfecting solution. Container 12 has an end which includes a substantially circular periphery defining an opening which is adapted to receive a lens retaining means. Cap 14 is releasably affixed to the open end of container 12 via mating threading 16 on the cap and container.

Cap 14 has elongated member 18 affixed thereto. Elongated member 18 supports article-retaining means 20, catalytic element-retaining means 22, and deformable sealing means 24. The catalyst element-retaining means holds catalytic element 26 beneath article-retaining means 20. Elongated member 18 extends into cavity 26 defined by container 12 when cap 14 is affixed to the container. The deformable sealing means is positioned between cap 14 and article-retaining means 20 to seal cavity 28 from the surroundings, and prevent liquid held within the cavity from leaking from the disinfection apparatus when the apparatus is tilted or turned upside down.

The deformable sealing means provides a normally closed, substantially liquid-impermeable seal for liquid held within the container. However, the sealing means is at least partially deformable, such that internal gas generated within the container will vent to a point outside the container by at least partially deforming a portion of the sealing means, thereby forming a passageway between a point inside said container to a point outside said container. The passageway may include a path through a loosely threaded cup-container connection or openings, such as circular holes, directly through the cap.

Figure 2A:
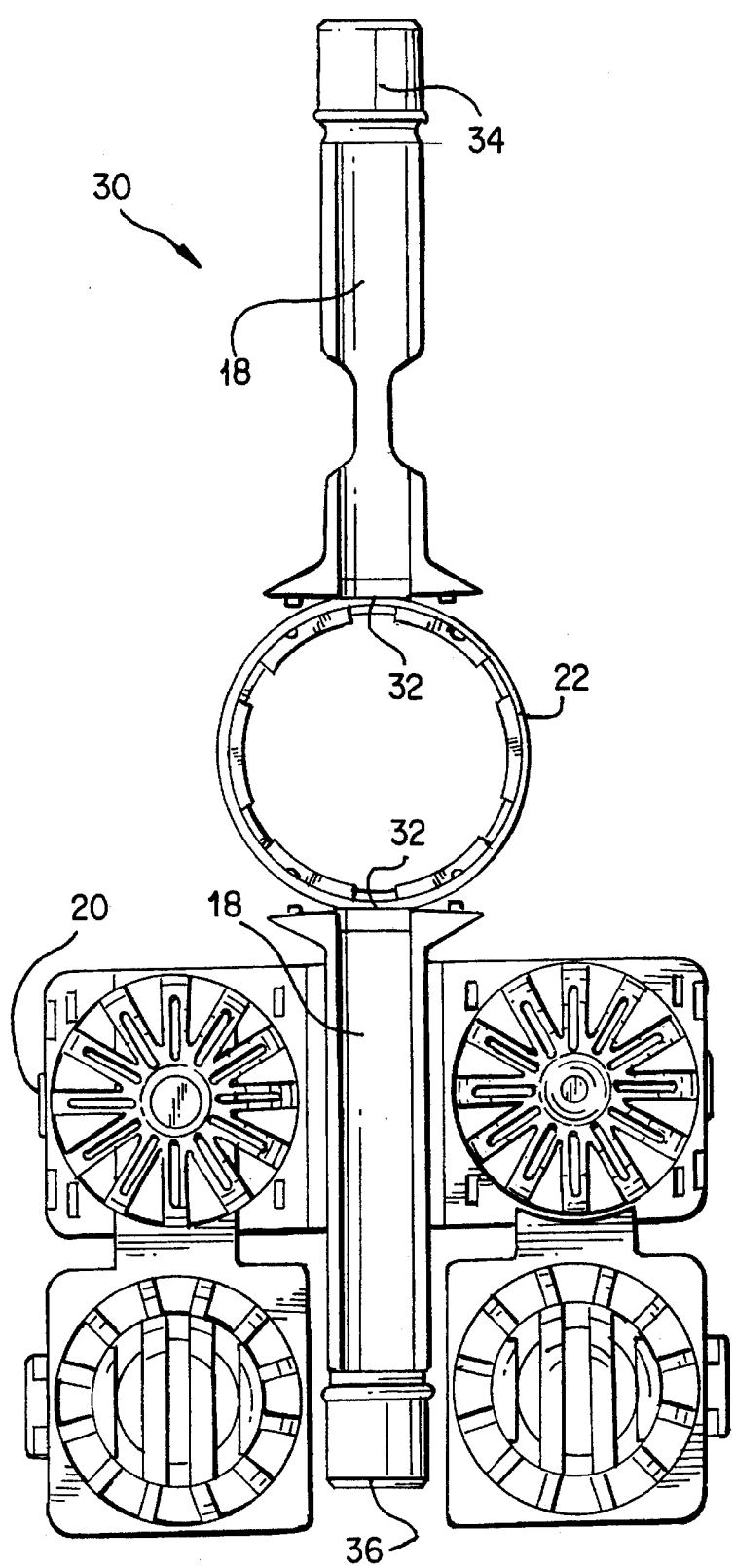
FIGS. 2a and 2b are side sectional views of one embodiment of an unassembled, molded member of the present invention which includes article- and catalyst-retaining means.
Figure 2B:
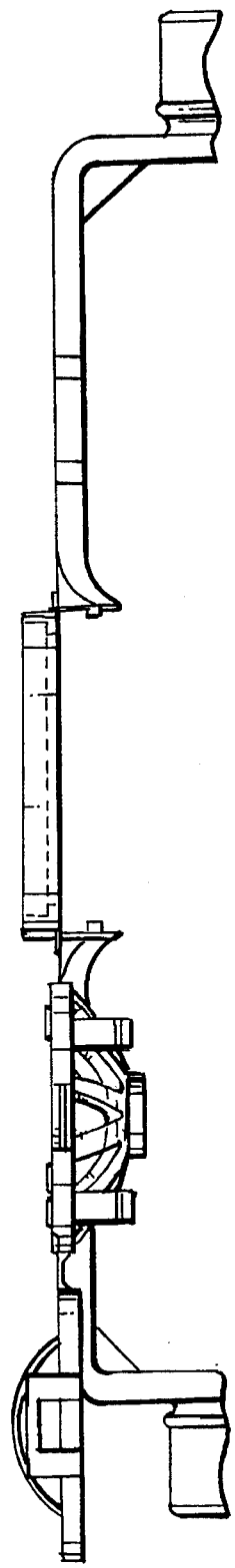

FIGS. 2a and 2b are side sectional views of one embodiment of an unassembled, molded member which includes article-retaining means 20, catalytic element-retaining means 22, and elongated member 18. In order to assemble molded member 30, first a catalytic element (not shown in FIGS. 2a and 2b) is inserted into catalytic element-retaining means. Then, elongated member 18 is folded at flexible joints 32 so that end 34 is positioned immediately adjacent end 36. Ends 34 and 36 are permanently affixed to one another by any means known in the art, including without limitation thereto, use of adhesives, use of pressure affixation methods, use of interference fit designs of the ends, or use of heat sealing methods.

Figure 3:
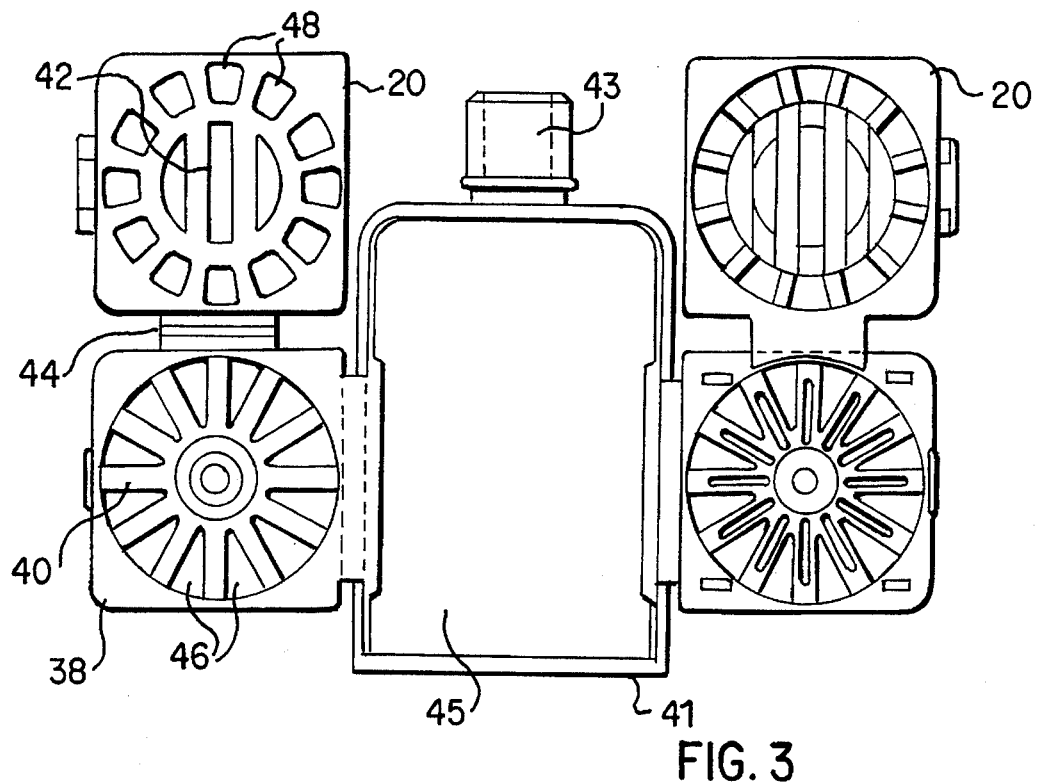
FIG. 3 is a side sectional view of an alternative embodiment of the molded member of the present invention which includes article- and catalyst-retaining means.

FIG. 3 is a side sectional view of an alternative molded member to the embodiment shown in FIGS. 2a and 2b. While the embodiment of FIGS. 2a and 2b requires a step of affixing end 34 to end 36 subsequent to molding, the FIG. 3 embodiment is a molded member which does not require a subsequent affixation step to form end 43. In this embodiment, article-retaining means 20 includes two holders which are shaped to hold ophthalmic lenses, especially contact lenses. Lens holder 38 includes a concave portion 40 and a convex portion 42 connected by a flexible joint 44. In use, a contact lens may be placed in concave portion 40, while convex portion 42 is rotated to a position immediately adjacent concave portion 40. The concave and convex portions are releasably affixed to one another, e.g., by interference fit or some form of snap fitting, to retain the lens during the disinfection cycle. Concave portion 40 and convex portion 42 include openings 46 and 48, respectively, to allow disinfecting solution to pass through to the lens retained therein.

A catalytic element is inserted into opening 45 of the FIG. 3 embodiment and dropped onto catalytic element-retaining means 41. The peripheral rim of the catalytic element-retaining means (See FIG. 7b) rests on the peripheral support of catalytic element-retaining means 41. Once the catalytic element is inserted into its resting position, the two article-retaining members are moved into position as shown in FIG. 4a and 4b, with the article-retaining means trapping the catalytic element from the side opposite the catalytic element retaining means 41.

Figure 4A:
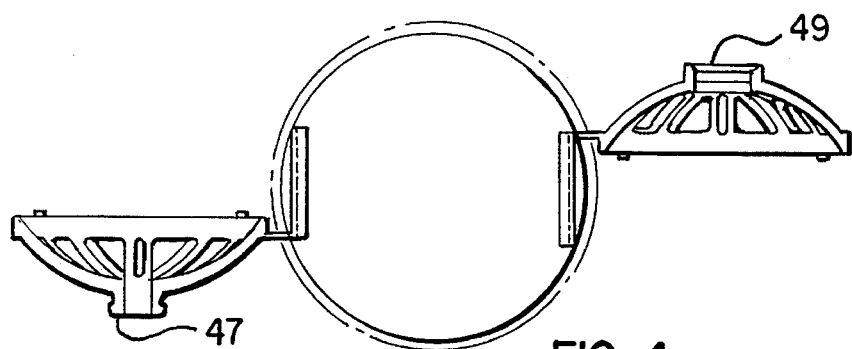
FIGS. 4a and 4b are bottom views of the molded member of FIG. 3.
Figure 4B:
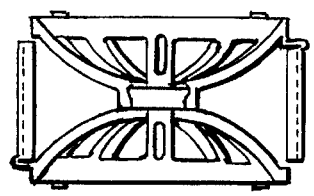

FIGS. 4a and 4b are bottom views of the molded member of FIG. 3. FIG. 4a illustrates the molded member with the contact lens holders in an open position, ready to receive contact lenses. FIG. 4b illustrates the molded member with contact lens holders releasably affixed to the molded member in a position which minimizes the cross-sectional area, so that the molded member and contact lenses may be easily inserted into the disinfection container. The contact lens holders are affixed to one another by an interference between male affixation member 47 on one contact lens holder and female affixation member 49 on the other contact lens holder. The interference fit is preferably sufficiently secure to prevent the consumer from manually separating the contact lens holders, so that the consumer is encouraged to recycle the entire assembly, i.e., molded member and catalytic element, at one time.

Figure 5A:
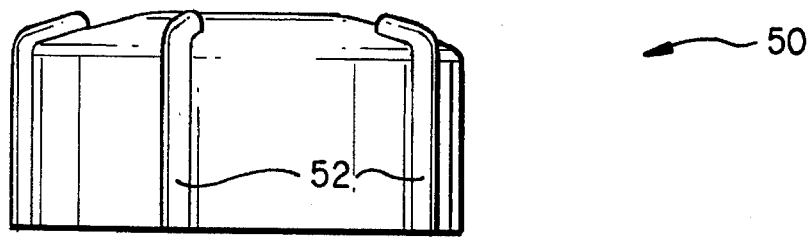
FIGS. 5a, 5b, 5c, and 5d are side, top, bottom and side sectional views, respectively, of one embodiment of the cap.
Figure 5B:
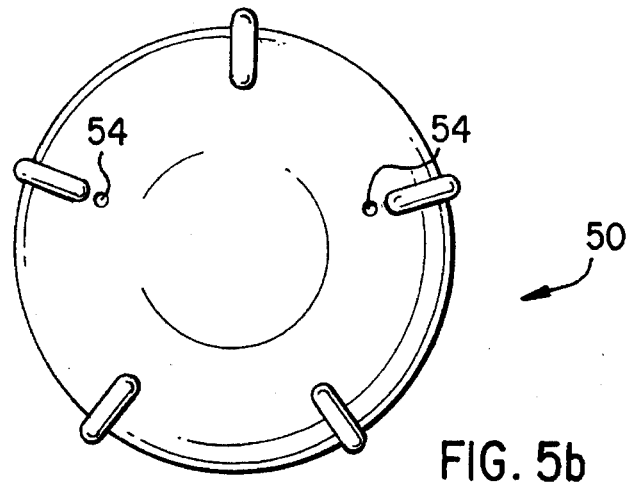

FIGS. 5a and 5b are side and top views of one embodiment of the cap, respectively. Cap 50 preferably includes grasping means such as ribs 52, as shown in FIG. 5a, which are raised from the surface of the cap an amount which promotes consumer convenience in grasping the cap. In the FIG. 5b embodiment, the cap also includes venting passageways which are openings extending through the cap. Cap 50 includes two substantially circular holes 54 extending through the cap, providing a passageway from a point inside the container to a point outside the container when the cap is affixed to the container.

Figure 5C:
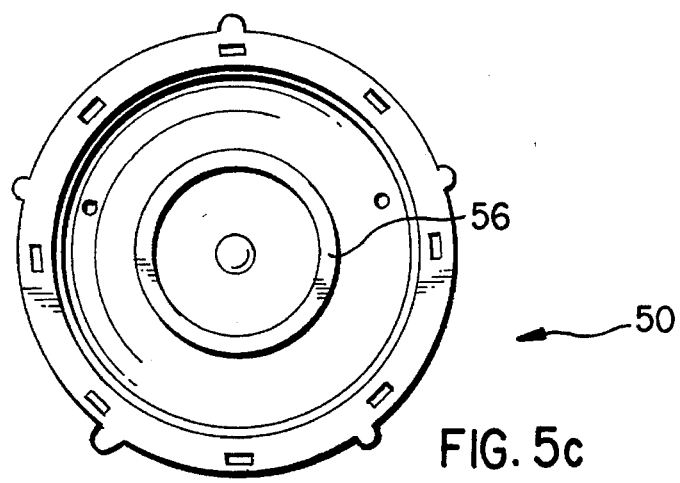
Figure 5D:
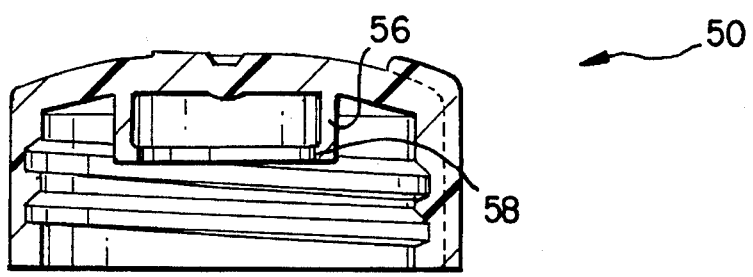

FIGS. 5c and 5d are bottom and side sectional views, respectively, of cap 50. Cap 50 includes a cylindrical-shaped affixation means 56 which extends substantially perpendicularly from the inside surface of cap 50. Affixation means 56 includes a peripheral lip 58 which extends inwardly from the end of the affixation means which is opposite the surface of cap 50. The sealing means is connected to the cap by affixation means 56.

Figure 6A:
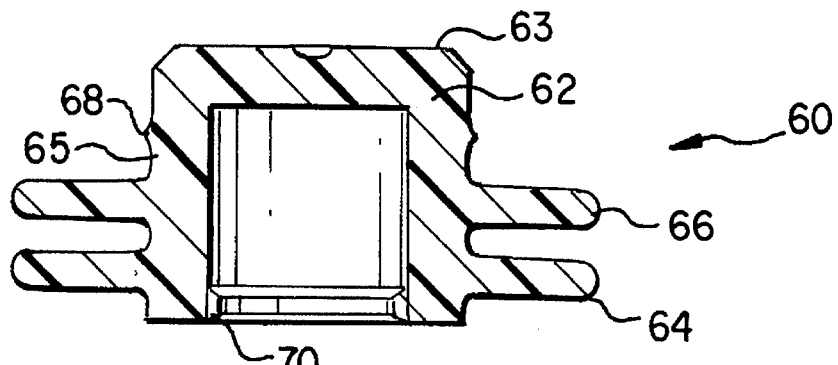
FIGS. 6a, 6b, and 6c are side sectional, top and side views, respectively, of one embodiment of the sealing means of the present invention.
Figure 6B:
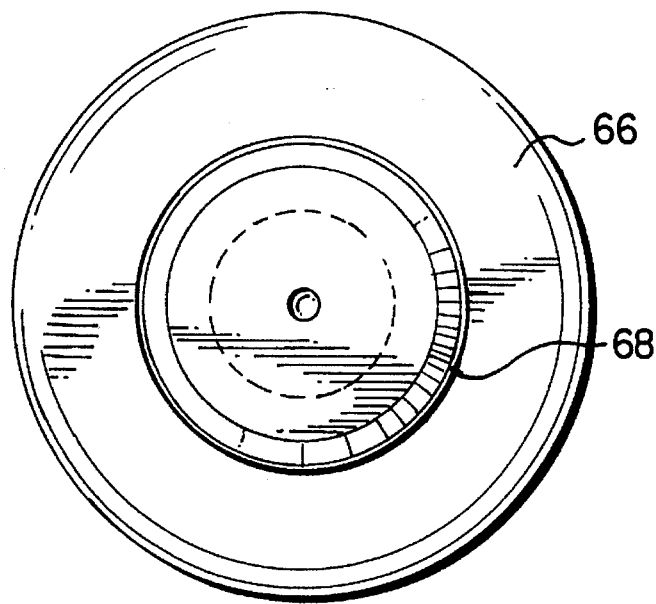
Figure 6C:
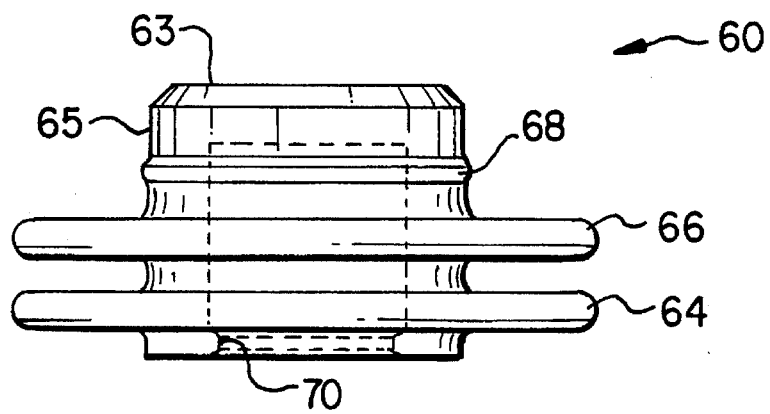

FIGS. 6a, 6b, and 6c are side sectional, top and side views of one embodiment of the sealing means of the present invention. Sealing means 60 includes cup-shaped housing 62 having a concave and a convex surface. The convex surface includes a substantially flat surface 63 which is adapted to mate with cap 50 and a substantially cylindrical wall 65. Two elongated rims 64 and 66 extend peripherally outward and substantially perpendicularly from the cylindrical wall of the convex surface of sealing means 60. Sealing means 60 further includes a lip 68 which extends peripherally outward from the cylindrical wall of the convex surface of sealing means 60, at a position between the flat surface 63 and rims 64 and 66. When the device is assembled, sealing means 60 is retained on cap 50 by an interference fit between sealing means lip 68 and cap lip 58.

Sealing means 60 is formed from a resiliently flexible material so that rims 64 and 66 may be deformed by internal pressure to provide a vent passageway between the sealing means and the container wall for venting. Thus, the seal is not formed within the cap, but is formed by intimate contact between sealing rims 64 and 66 and the container walls. While sealing means 60 may be formed from a wide variety of materials, preferred materials include polypropylene and polyethylene.

The sealing means of the present invention provides a substantially liquid impermeable seal with the interior of the container walls to form a sealed chamber for liquid retention. When gas in the sealed chamber causes the internal pressure to reach a predetermined value in excess of the external ambient pressure, the sealing means rims flex or deform, at least partially, to allow gas to pass. The gas may then vent outside the apparatus through openings in the cap or through the mating threads of the cap-container connection.

The sealing means of the present invention presents clear advantages over the prior art. One advantage is that the sealing means includes at least two rims, both of which provide protection from solution leakage or spills. If one of the rims becomes damaged (e.g., torn) or inadvertently held open (e.g., by debris on the container walls), the other rim still provides completely independent sealing and venting functions. Another advantage of the present sealing means is that the double rim design prevents any leakage from any solution which inadvertently passes the first rim. For example, if the apparatus is placed in a travel container and shaken during travel, increased disinfectant decomposition rates and foaming may result. Alternatively, if the apparatus is placed upside down during the disinfectant decomposition process, solution may conceivably be forced past the first rim. In either of these instances, the second sealing rim provides additional protection to keep the solution from leaking out of the disinfection apparatus.

The catalytic element includes a thin molded substrate and a catalytic coating deposited on the substrate. The substrate is preferably an inexpensive plastic material, such as poly(ethylene terephthalate), also known as PET. The preferred catalytic coating is platinum or a platinum-containing alloy, because platinum catalyzes the decomposition of hydrogen peroxide into water and oxygen. The coating may be deposited by a number of methods known in the art, including dip coating and ion beam deposition methods. A preferred method of coating the substrate material is by ion beam-assisted deposition. Thus, a preferred catalytic element has a PET substrate which is coated or impregnated with platinum metal.

The catalytic element is preferably of a shape which lends itself to inexpensive and efficient mass production by vacuum forming. Thus, the catalytic element preferably has a convex surface and a concave surface. The catalytic element should have a base portion and a side wall portion which extends from the peripheral edge of the base portion, with the side walls having either a cylindrical or conical shape. In addition, the catalytic element preferably has protrusions or extensions which increase surface area without either substantially increasing the volume the element must occupy or substantially increasing the difficulty of manufacture.

The catalytic element should also be shaped to promote good fluid flow and minimize "dead space" (i.e., areas of little or no flow) during the disinfectant decomposition process. Therefore, the catalytic element preferably includes a plurality of holes therethrough, with the holes being located to facilitate improved flow regimes. Finally, the catalytic element should have a means for affixing the catalytic element to the disinfection apparatus.

In a preferred embodiment, the catalytic element has a truncated cone shape. Thus, the catalytic element has a circular flat surface with a conical wall extending outwardly from the edge of the circular flat surface. The angle which the conical wall extends from the flat surface has an impact on both the flow during the decomposition of the disinfectant and the catalytic metal deposition process. If the angle of the wall is too steep, deposition of metal (e.g., platinum) on the wall is very difficult. On the other hand, angles which are too large (i.e., approaching a flat sheet) tend to cause gas bubbles to remain adhered to the wall during the disinfection process. The adhered bubbles prevent disinfectant from efficiently contacting the catalyst, thereby slowing the decomposition process. Therefore, the angle between the conical portion and flat bottom portion of the catalyst is preferably about 30 to 60 degrees.

Also, the catalytic coating is preferably only deposited on the inner walls of the catalyst substrate material. Coating only the inner walls of the catalyst substrate ensures that gas from disinfectant decomposition is generated only on the concave interior portion of the catalytic element. A current is then generated as the gas bubbles are released from the interior of the catalytic element and move towards the top of the disinfectant container. Solution from beneath the catalytic element passes through the openings in the bottom of the catalytic element to replace the gas bubbles which are released from the inside. Thus, gas bubbles moving upward in the interior of the container cause an interior upward solution flow and a downward solution flow near the container walls. In contrast, if catalytic material were deposited on the exterior of the catalytic element, decomposition gas bubbles would form on, and be released from, the exterior of the catalytic element, thereby opposing the previously-described current. Therefore, the catalytic element is preferably coated only on the interior surfaces in order to promote good mixing and minimize the time required to decompose the disinfectant.

Figure 7A:
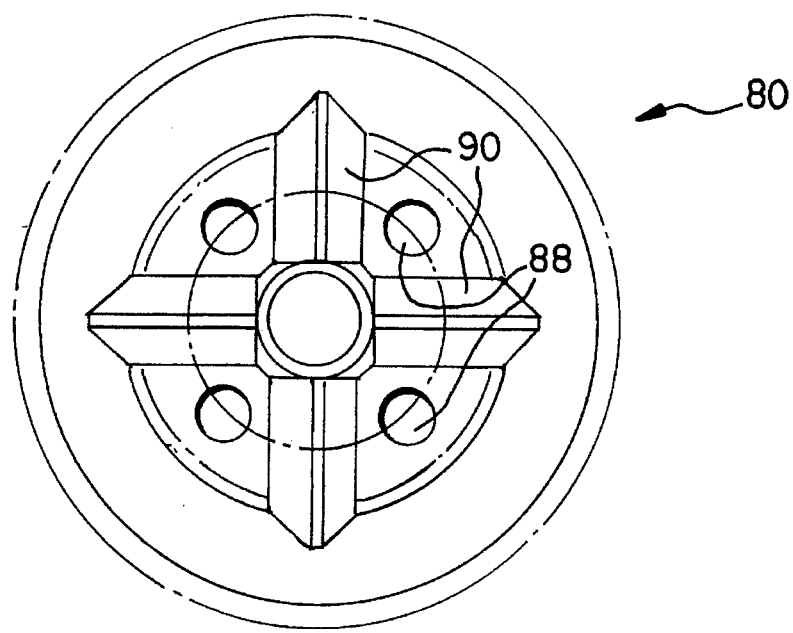
FIGS. 7a and 7b are bottom and side sectional views of one embodiment of the catalytic element of the present invention.
Figure 7B:
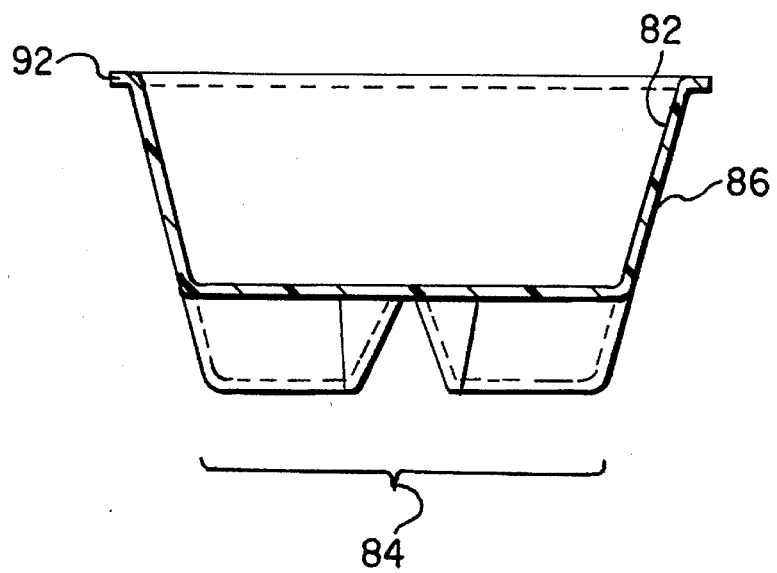

FIGS. 7a and 7b are bottom and side sectional views of one embodiment of the catalytic element of the present invention. Catalytic element 80 has a interior concave surface 82 and an exterior which includes a base portion 84 and walls 86 extending in a conical fashion from bottom 84. Catalytic element 80 also includes a plurality of holes 88 through bottom surface 84. Bottom surface 84 includes raised portions 90 which add surface area to the catalytic element without adding substantially to the difficulty of manufacturing the catalytic element or to the volume required by the catalytic element when placed in the container.

Catalytic element 80 also includes rim 92 which extends outwardly along the peripheral edge of the catalytic element. The catalytic element is retained within the assembled elongated member when rim 92 rests within catalytic element-retaining means 22 (See FIG. 1).

Figure 8:
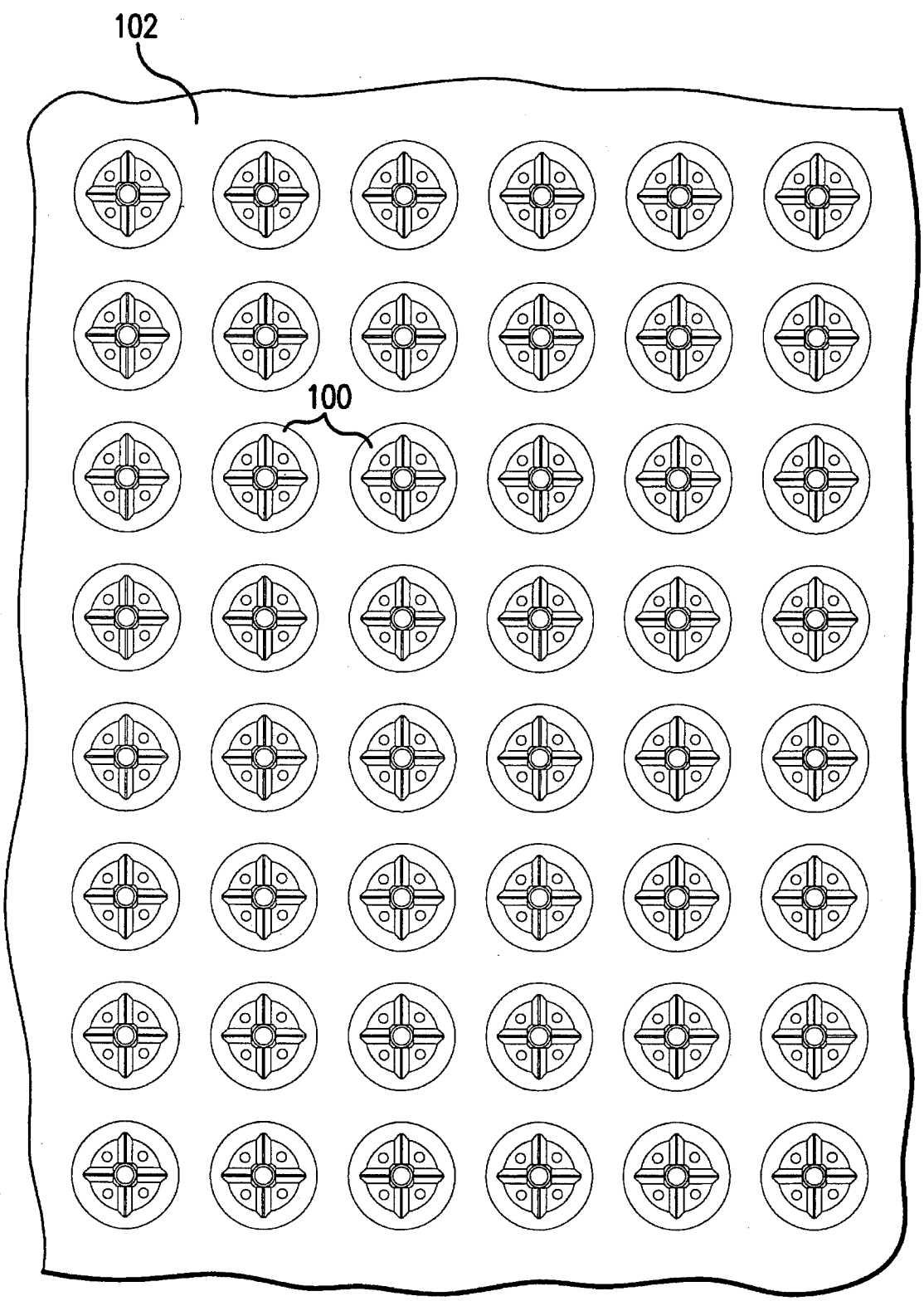
FIG. 8 is a bottom view of a molded sheet of catalytic elements of FIGS. 7a and 7b.

The substrate of the catalytic element is a flexible material which has sufficient rigidity to give the catalytic element a definite shape. Preferably, the substrate is formed in an efficient, inexpensive vacuum forming process. FIG. 8 is a bottom view of a molded sheet of catalytic element substrates having the shape of the catalytic elements of FIGS. 7a and 7b. A plurality of catalytic element 100 are vacuum formed in a sheet of substrate material 102. The catalytic element substrates may then be punched out or cut out of the sheet 102.

Coating of the catalytic elements may occur prior to or subsequent to the removal of the shaped catalytic element substrates from the material sheet. In a preferred embodiment, the catalytic elements are vacuum formed and coated with catalyst in a semi-batch or continuous process. For example, the catalytic element formation process may include the steps of (a) feeding a continuous sheet of substrate material into a vacuum forming chamber, (b) vacuum forming a desired catalytic element shape in the substrate material, (c) feeding the continuous sheet into a coating chamber, (d) coating at least one surface of the shaped catalytic element substrate to form a catalytic element, and (e) removing a catalytic element from the sheet. While all surfaces of the catalytic element may be coated, it is preferably to have only the interior surface of the shaped catalytic element substrate coated with catalyst material.

It should be noted that the methods of affixing components of the disinfecting apparatus to one another may be selected from a wide variety of affixation methods known in the art and described generally herein. However, "releasably affixing" one component to another refers to the affixing of components in a manner that allows the components to be separated from, and re-affixed to, one another many times without substantially damaging the components or the affixation means. "Permanently affixing" one component to another refers to methods of affixing components such that separation of the components results in substantial damage to one or more of the components, likely to render the components or affixation means inoperable.

The invention has been described in detail, with reference to certain preferred embodiments, in order to enable the reader to practice the invention without undue experimentation. However, a person having ordinary skill in the art will readily recognize that many of the components and parameters may be varied or modified to a certain extent without departing from the scope and spirit of the invention. Furthermore, titles, headings, or the like are provided to enhance the reader's comprehension of this document, and should not be read as limiting the scope of the present invention. Accordingly, the intellectual property rights to this invention are defined only by the following claims and reasonable extensions and equivalents thereof.

That which is claimed is:

1. A disinfection device, comprising:

(a) a container adapted to receive a disinfecting solution, said container having at least one end which includes a substantially circular periphery defining an opening which is adapted to receive a lens retaining means;

(b) a cap adapted to be releasably affixed to said container at said open end;

(c) an elongated member affixed to said cap, wherein said elongated member extends into said container when said cap is affixed to said container;

(d) means for retaining articles to be disinfected, said article-retaining means being affixed to said elongated member, whereby said article-retaining means extends into said container when said cap is affixed to said container;

(e) means for releasably sealing said container along the interior periphery of the substantially circular container, thereby providing a normally liquid-impermeable seal, wherein said sealing means is affixed to said elongated member interposed between said article-retaining means and said cap, whereby said sealing means is at least partially deformable, such that internal gas generated within said container will vent to a point outside said container, when the internal pressure reaches a predetermined pressure in excess of the external pressure, by at least partially deforming a portion of said sealing means, thereby forming a passageway between a point inside said container to a point outside said container; and (f) a catalytic element affixed to said elongated member, wherein said catalytic element is positioned inside said sealed container when said cap is affixed to said container.

2. A device of claim 1, wherein said cap includes at least one hole therethrough, such that when internal gas pressure exceeds a predetermined pressure beyond the external atmospheric pressure, gas will vent by at least partially deforming said sealing means, passing between said sealing means and said container wall, and passing through said hole in said cap.

3. A device of claim 1, wherein said cap is affixed to said container by mating threads on said cap and said container, wherein said mating threads provide sufficient space therebetween to allow gas to vent through the space between said mating threads when the pressure inside said sealed container exceeds said predetermined pressure.

4. A device of claim 1, wherein said catalytic element has a concave surface and a convex surface.

5. A device of claim 4, wherein said concave surface of said catalytic element faces said article-retaining means.

6. A device of claim 1, wherein said catalytic element is permanently affixed to said elongated member, such that removal of said catalytic element will damage said catalytic element-retaining means and render said catalytic element-retaining means inoperable.

7. A device of claim 1, wherein said article is an ophthalmic lens.

8. A device of claim 7, wherein said ophthalmic lens is a contact lens.

9. A device of claim 1, wherein said catalytic element comprises:

(a) a catalyst substrate, including:

(1) a base portion, (2) a side wall portion extending from the peripheral edge of the base portion, wherein said portions define an inner concave surface and an outer convex surface, and (3) a means for affixing said catalytic element to a catalytic element supporting member; and (b) a coating of catalytic material deposited on at least a portion of at least one of said surfaces, which catalytic material catalyzes the decomposition of a said species in solution.

10. A device of claim 1, wherein said sealing means comprises:

(a) a housing having an internal and an external surface;

(b) at least two elongated rims extending outwardly from said external surface a distance which is sufficient for said rims to contact the internal surfaces of said container to establish a sealed chamber with said container, which sealed chamber is substantially liquid impermeable, wherein said rims are sufficiently flexible to at least partially deform to allow gas to vent from said chamber when the internal pressure of the chamber exceeds a predetermined amount beyond the pressure outside said rims, and wherein said rims are sufficiently resilient to return to contact said internal surfaces of said container after venting, thereby reestablishing said sealed chamber.

11. An assembly for retaining ophthalmic lenses, sealing a container, and retaining a catalytic element, said assembly comprising:

(a) a cap including a means for affixing said cap to a container to be used with said assembly;

(b) an elongated support member affixed to said cap;

(c) means for sealing a container, said sealing means being affixed to said elongated support member, said means being capable of forming a substantially liquid impermeable, gas permeable chamber with a container along an interior periphery of the container;

(d) means for retaining contact lenses affixed to said elongated support member;

(e) a means for retaining a catalytic element, said catalytic element-retaining means being affixed to said elongated support member; and (f) a catalytic element retained within said catalytic element-retaining means.

12. An assembly of claim 11, wherein said sealing means is capable of forming a seal with interior walls of said container.

13. An assembly of claim 11, wherein said sealing means is positioned between said lens-retaining means and said cap.

14. An assembly of claim 13, wherein said lens-retaining means is positioned between said sealing means and said catalytic element-retaining means.

* * * * *